April 24, 1962 M. L. MEILLAND Plant Pat. 2,140
ROSE PLANT
Filed March 28, 1961
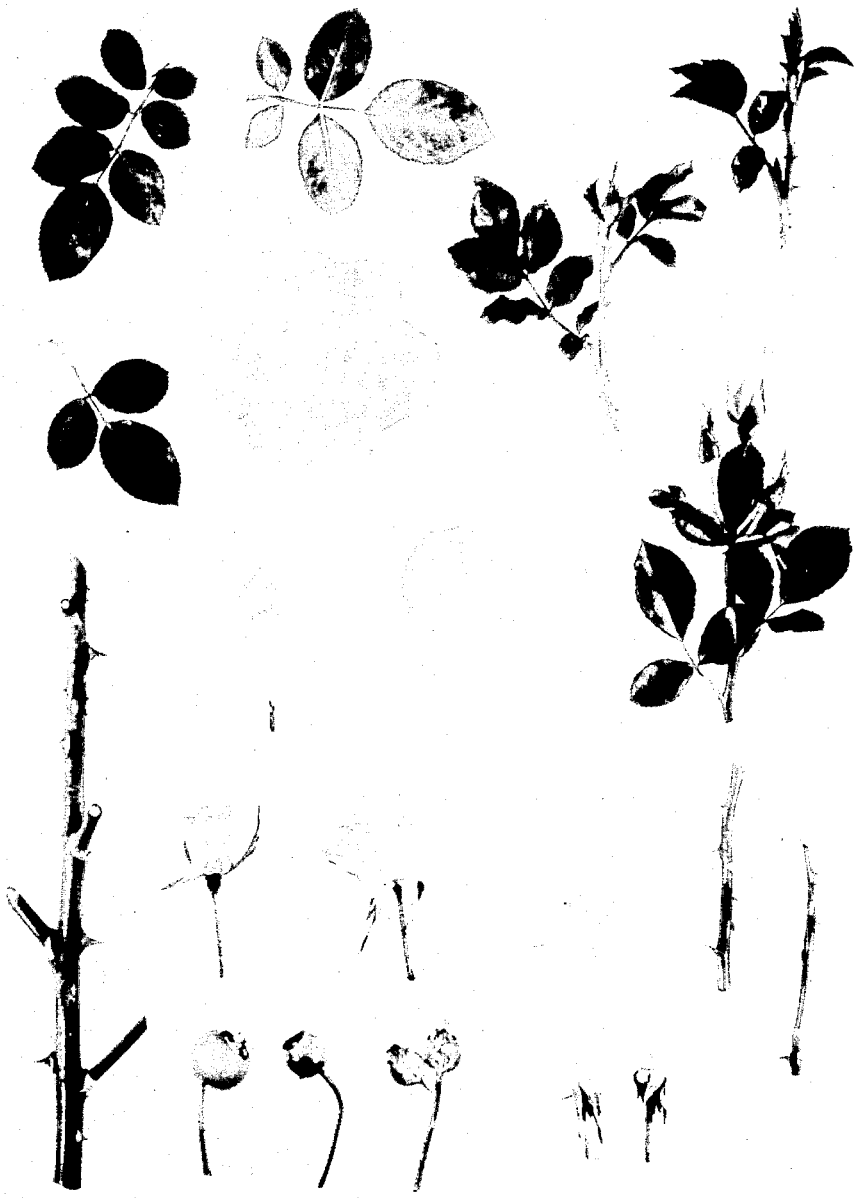
INVENTOR
Marie Louise Meilland
BY Robb & Robb
ATTORNEYS United States Patent Office Plant Pat. 2,140
Patented Apr. 24, 1962

2,140
ROSE PLANT

Marie Louise Meilland, Cap d'Antibes, Alpes Maritimes, France, assignor to The Conard-Pyle Company, West Grove, Pa., a corporation of Pennsylvania Filed Mar. 28, 1961, Ser. No. 98,994
Claims priority, application France May 31, 1960
1 Claim. (Cl. 47—61)

The present invention relates to a new and distinct variety of rose plant of the hybrid polyantha class, which was originated by me by crossing two unnamed and unpatented seedlings derived from crossing the variety known as "Goldilocks" (U.S. Plant Patent No. 672) × the variety known as "Fashion" (U.S. Plant Patent No. 789). As the result of this breeding, I have produced a new rose variety having the following outstanding features which represent a unique combination and which distinguish the new variety from its parents, as well as from all other varieties of which I am aware:

(1) An attractive and compact habit of bush growth of slightly less than average height;

(2) Attractive and abundant foliage which clothes the plant well;

(3) Good continuity of bloom;

(4) An attractive and unusual flowery form;

(5) A light sweetbrier flower fragrance; and (6) A distinctive and unusual general color tonality of the flowers corresponding to Saturn Red, with Mimosa Yellow center when the flowers first open, and changing to Fire Red as the flowers mature.

Asexual reproduction of the new variety by budding, as performed at West Grove, Pennsylvania, U.S.A., and also in France, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Color Chart of the Royal Horticultural Society, except where general color terms of ordinary dictionary significance are obivous:

Type: Hardy; bush; outdoor; seedling; for garden decoration.

Class: Hybrid polyantha.

Breeding: Seedling.

*Seed parent.*—An unnamed seedling of "Goldilocks" × "Fashion."

*Pollen parent.*—Another unnamed seedling of "Goldilocks" × "Fashion."

Propagation: Holds its distinguishing characteristics through succeeding propagations by budding.

*Flower*

*Locality where grown and observed*: West Grove, Pennsylvania, U.S.A.

*Filowers borne*: Several to stem; in regular cluster; on stems of medium length and normal strength.

*Quantity of bloom*: Abundant, outdoors.

*Continuity*: Continuous.

*Fragrance*: Slight. Nature—sweetbrier.

Bud:

*Peduncle.*—Medium length; medium caliper; erect; rough; with numerous glandular trichomes. Color—Fern Green, Plate 0862, overlaid with Garnet Brown, Plate 00918/3 where exposed to sun.

*Before calyx breaks.*—Size—medium. Form—medium length; pointed; with a conspicuous neck; with foliaceous appendages on the surface of the bud; with bristle-like foliaceous parts extending beyond the tip of the bud equal to ½ or more of its length.

*As calyx breaks.*—Color—near Brick Red, Plate 016.

*As first petal opens.*—Size—from small to medium. Form—medium length; ovoid. Color: outside—near Poppy Red, Plate 16/2, bordered by Shrimp Red, Plate 616 on the sides of the petals, and with the base of the petals Mimosa Yellow, Plate 602; inside—Orange, Plate 12, sometimes tinted with Fire Red, Plate 15/2 where exposed to sunlight, and with base of petals Aureolin, Plate 3.

*Opening.*—Opens up well.

Bloom:

*Size (when fully open).*—Medium; from 2½ inches to 3 inches.

*Petalage.*—Semi-double; from 10 to 15 petals.

*Form.*—High-centered at first, but becoming flat; petals at first being rolled inward, but later becoming loosely rolled outward at maturity.

Petals: Medium thickness; leathery; with inside satiny and outside shiny. Shape: outer—roundly ovate; inner—ovate.

This description of a newly opened flower was made from a rose grown outdoors in the month of August at West Grove, Pennsylvania, U.S.A.

*Color.*—Outer petal: outside surface—near Burnt Orange, Plate 014/1, often streaked or blotched with Chrysanthemum Crimson, Plate 824/2, and with base of petal Mimosa Yellow, Plate 602/1; inside surface—Orange, Plate 12 at outer margin, grading to Saturn Red, Plate 13/1, and with base of petal Aureolin, Plate 3. Inner petal: outside surface—near Burnt Orange, Plate 014, often veined and streaked with Mimosa Yellow, Plate 602/1, and with base of petal Mimosa Yellow, Plate 602; inside surface—Burnt Orange, Plate 014 at outer margin, bordering Saturn Red, Plate 13/1, and with base of petal Aureolin, Plate 3.

This description was made from a rose that was open for three (3) days outdoors in the month of August at West Grove, Pennsylvania, U.S.A.:

*Color.*—Outer petal: outside surface—Fire Red, Plate 15/2, veined with Mimosa Yellow, Plate 602/2, and with base of petal Mimosa Yellow, Plate 602/1; inside surface—near Nasturtium Red, Plate 14/2, overlaid with Blood Red, Plate 820 over upper margin of petal, and with base of petal Mimosa Yellow, Plate 602. Inner petal: outside surface—near Fire Red, Plate 15/2, veined with Mimosa Yellow, Plate 602/3, and with base of petal Mimosa Yellow, Plate 602/2; inside surface—between Fire Red, Plate 15/1 and Fire Red, Plate 15/2, with base of petal Mimosa Yellow, Plate 602/1.

*General color effect.*—Newly opened flower—Saturn Red, Plate 13/1, with center of bloom Mimosa Yellow, Plate 602/1. 3-days open—between Fire Red, Plate 15/1 and Fire Red, Plate 15/2.

*Behavior.*—Drop off cleanly.

*Flower longevity.*—On bush in garden—4 days in August. Cut roses grown outdoors and kept at livingroom temperatures—3 or 4 days in August.

*Reproductive Organs*

Stamens: Many; arranged regularly about pistils; mixed with petaloids.

Filaments: Medium length; most with anthers. Color—Canary Yellow, Plate 2.
Anthers: All open at once; medium size; occasionally an anther fused with a petaloid. Color—Lemon Yellow, Plate 4.
Pollen: Abundant. Color—Lemon Yellow, Plate 4.
Pistils: Medium number.
Styles: Uneven; medium length; medium caliper; bunched.
Stigma: Color—white yellow.
Ovaries: All enclosed in receptacle.
Hips: Globular; with inconspicuous neck; smooth; walls medium fleshy. Color—reddish.
Sepals: Permanent; medium length; spear-shaped.
Seeds: Medium number; medium size.

*Plant*

Foliage:

*Leaves.*—Compound of 5 or 7 leaflets; leathery.

*Leaflets.*—Shape—ovoid, with apex acute. Base—obtuse. Margin—simply serrate.

*Color.*—Mature: upper surface—near Ivy Green, Plate 0001060/1; under surface—near Sage Green, Plate 000861/1, veined and lightly overcast with Erythrite Red, Plate 0027. Young: upper surface—nearly Parsley Green, Plate 00962/1, thinly margined with Oxblood Red, Plate 00823; under surface—near Fern Green, Plate 0862, irregularly overlaid with Oxblood Red, Plate 00823/3.

*Rachis (the supporting stem of the compound leaf).*—Medium caliper. Upper side—grooved; hairy. Under side—generally smooth.

*Stipules.*—From medium length to long; with points of medium length turning out at an angle of 45°.

*Disease resistance.*—Comparable to that of the average variety grown under the same cultural conditions at West Grove, Pennsylvania, U.S.A.

Growth:

*Habit.*—Bushy; much-branched.

*Growth.*—Vigorous.

*Canes.*—Medium caliper.

*Main stems.*—Bright. Color—slightly darker than Lettuce Green, Plate 861. Prickles—several; color—near Garnet Brown, Plate 00918/3. Hairs—none.

*Branches.*—Bright. Color—Lettuce Green, Plate 861. Prickles—several; color—near Oxblood Red, Plate 00823/2. Hairs—none.

*New shoots.*—Dull. Color—Lettuce Green, Plate 861/2, overlaid with Oxblood Red, Plate 00823/3. Prickles—several; color—near Oxblood Red, Plate 00823/2. Hairs—none.

I claim:

A new and distinct variety of rose plant of the hybrid polyantha class, substantially as herein shown and described, characterized particularly as to novelty by the unique combination of an attractive and compact habit of bush growth of slightly less than average height, attractive and abundant foliage which clothes the plant well, good continuity of bloom, an attractive and unusual flower form, a light sweetbrier flower fragrance, and a distinctive and unusual general color tonality of the flowers corresponding to Saturn Red with Mimosa Yellow center when the flowers first open, changing to Fire Red as the flowers mature.

No references cited.